(12) United States Patent
Yokoi et al.

(10) Patent No.: US 8,491,464 B2
(45) Date of Patent: Jul. 23, 2013

(54) IN-VIVO INFORMATION ACQUIRING APPARATUS, IN-VIVO INFORMATION ACQUIRING SYSTEM, AND IN-VIVO INFORMATION ACQUIRING METHOD

(75) Inventors: Takeshi Yokoi, Hino (JP); Katsumi Hirakawa, Sagamihara (JP); Akio Uchiyama, Yokohama (JP); Shinsuke Tanaka, Hachioji (JP); Hironobu Takizawa, Hachioji (JP); Manabu Fujita, Hino (JP)

(73) Assignees: Olympus Corporation (JP); Olympus Medical Systems Corp. (JP)

( * ) Notice: Subject to any disclaimer, the term of this patent is extended or adjusted under 35 U.S.C. 154(b) by 993 days.

(21) Appl. No.: 11/571,510

(22) PCT Filed: Jul. 10, 2006

(86) PCT No.: PCT/JP2006/313703
§ 371 (c)(1),
(2), (4) Date: Nov. 13, 2008

(87) PCT Pub. No.: WO2007/007724
PCT Pub. Date: Jan. 18, 2007

(65) Prior Publication Data
US 2009/0076325 A1  Mar. 19, 2009

(30) Foreign Application Priority Data
Jul. 8, 2005 (JP) .................. 2005-200885

(51) Int. Cl.
*A61B 1/00* (2006.01)
(52) U.S. Cl.
USPC ............ 600/109; 600/102; 600/160; 600/424
(58) Field of Classification Search
USPC ................. 600/103, 117, 118, 371, 109–114, 600/160–177, 407, 424
See application file for complete search history.

(56) References Cited

U.S. PATENT DOCUMENTS 2,773,502 A * 12/1956 Kaslow et al. .................. 604/57
3,528,429 A *  9/1970 Beal et al. ..................... 600/367
(Continued)

FOREIGN PATENT DOCUMENTS
EP    1 685 871    8/2006
JP    4-347138    12/1992
(Continued)

OTHER PUBLICATIONS

Search Report issued on Oct. 3, 2006 in connection with corresponding PCT patent application No. PCT/JP2006/313703 (WO 2007/007724).

(Continued)

*Primary Examiner* — Matthew J Kasztejna
*Assistant Examiner* — Ryan Henderson
(74) *Attorney, Agent, or Firm* — Ostrolenk Faber LLP (57) ABSTRACT

To stably and properly monitor an inside of a body by using an easily operable placement technique, a capsule endoscope 101 to be swallowed from an oral cavity 200 to acquire in-vivo information of a subject 201 and to wirelessly output for a transmission of the in-vivo information to an outside of a body, a string member 103 that is connected to the capsule endoscope 101 for positioning the capsule endoscope 101 at a gastric cardia 202, and a fixing portion 104 that is a portion of the string member 103, is provided on a position with which a length from the capsule endoscope 101 corresponds to a length from the gastric cardia 202 to the inside of an esophageal region 203 for fixing the string member 103 that has located the capsule endoscope 101 at the gastric cardia 202 to the inside of the esophageal region 203 by an endoscopic fixture are included. As a result, the capsule endoscope 101 is placed at a position of the gastric cardia 202 where an entire inside of the stomach is easily inspected, and the capsule endoscope 101 itself can easily be placed inside the esophageal region by using the fixing portion 104.

14 Claims, 10 Drawing Sheets

U.S. PATENT DOCUMENTS

| | | | | |
|---|---|---|---|---|
| 5,611,787 | A * | 3/1997 | Demeter et al. | 604/270 |
| 5,738,110 | A * | 4/1998 | Beal et al. | 600/582 |
| 6,285,897 | B1 | 9/2001 | Kilcoyne et al. | 600/350 |
| 6,285,977 | B1 | 9/2001 | Miyazaki | 703/26 |
| 6,475,145 | B1 * | 11/2002 | Baylor | 600/309 |
| 7,245,954 | B2 * | 7/2007 | Glukhovsky | 600/350 |
| 7,824,347 | B2 * | 11/2010 | Imran et al. | 600/593 |
| 2003/0181788 | A1 * | 9/2003 | Yokoi et al. | 600/160 |
| 2005/0043601 | A1 * | 2/2005 | Kilcoyne et al. | 600/361 |
| 2005/0085697 | A1 | 4/2005 | Yokoi et al. | 600/160 |
| 2005/0158246 | A1 | 7/2005 | Takizawa et al. | 424/10.1 |
| 2005/0165272 | A1 * | 7/2005 | Okada et al. | 600/114 |
| 2005/0183733 | A1 * | 8/2005 | Kawano et al. | 128/899 |
| 2006/0189846 | A1 * | 8/2006 | Huang et al. | 600/160 |
| 2006/0195014 | A1 * | 8/2006 | Seibel et al. | 600/102 |
| 2006/0247720 | A1 * | 11/2006 | Starkebaum | 607/40 |

FOREIGN PATENT DOCUMENTS

| | | |
|---|---|---|
| JP | 05-023322 | 2/1993 |
| JP | H5-23322 | 2/1993 |
| JP | 06-063051 | 3/1994 |
| JP | 6-114036 | 4/1994 |
| JP | 6-142081 | 5/1994 |
| JP | H6-63051 | 8/1994 |
| JP | 2004-305593 | 11/2004 |
| JP | 2005-103092 | 4/2005 |
| JP | 2005-103130 | 4/2005 |
| WO | WO 2005/032352 | 4/2005 |
| WO | WO 2005/032644 | 4/2005 |

OTHER PUBLICATIONS

Search Report issued by European Patent Office and received by applicant on May 18, 2012 in connection with corresponding EP patent application No. EP 06 780 925.1.

International Search Report PCT/JP2006/313703 dated Sep. 2006.

* cited by examiner

IN-VIVO INFORMATION ACQUIRING APPARATUS, IN-VIVO INFORMATION ACQUIRING SYSTEM, AND IN-VIVO INFORMATION ACQUIRING METHOD

CROSS REFERENCE TO RELATED APPLICATION

The present application is a 35 U.S.C. §§371 national phase conversion of PCT/JP2006/313703, filed 10 Jul. 2006, which claims priority of Japanese Patent Application No. 2005-200885 filed 8 Jul. 2005, which is herein incorporated by reference.

TECHNICAL FIELD

The present invention relates to an in-vivo information acquiring apparatus, an in-vivo information acquiring system, and an in-vivo information acquiring method that are suitable for, for example, monitoring an existence of a bleeding site inside a stomach.

BACKGROUND ART

Recently, an endoscopic surgical procedure such as an endoscopic mucosal resection (EMR) and an endoscopic submucosal dissection (ESD) for an inside of a stomach has become available with the improvement of an endoscopic technology. After the endoscopic surgical procedure of the inside of the stomach, bleeding in a surgical site is stopped; however, because there is a possibility that the surgical site bleeds again at night, it is required to monitor an existence of the bleeding. Conventionally, as a method of monitoring the existence of the bleeding inside the stomach, a tube with a continuous length from the inside of the stomach to the outside of a body of a patient is inserted from a nose or a mouth and placed inside the stomach to monitor whether blood comes out of the body through the tube.

As a technology for detecting a status of the inside of a body cavity, for example, a technology for placing an indwelling capsule at around a pyloric by attaching a string to the pH-sensor indwelling capsule and fixing the end portion of the string to a region around teeth or a mouth is disclosed according to Patent Document 1. Patent Document 2 discloses a technology for sensing a physiological parameter of the inside of an esophageal region by placing a sensor capsule to a sensing target region inside the esophageal region of an examinee. Patent Document 3 discloses a technology for fixing a medical capsule to the inside of the body cavity by attaching a clip to the medical capsule and by clipping body tissue inside the body cavity by the clip.

Patent Document 1: Japanese Patent Application Laid-Open No. H6-63051
Patent Document 2: U.S. Pat. No. 6,285,977 Specification
Patent Document 3: Japanese Patent Application Laid-Open No. H5-23322

DISCLOSURE OF INVENTION

Problem to be Solved by the Invention

However, with the conventional method of monitoring the existence of the bleeding, because the tube is being inserted from the stomach to the nose or the mouth, there increases patient discomfort and there is a defect that the bleeding cannot be detected unless severe bleeding occurs.

The technologies disclosed in Patent Documents 1 to 3 are not desired for monitoring the existence of the bleeding inside the stomach, and therefore, not suitable for checking the existence of the bleeding inside the stomach without difficulty. For example, with the technology in Patent Document 1, a monitored region inside the stomach is limited to a surrounding region of the pyloric region, the sensor capsule is not fixed but can be moved in accordance with a movement of the oral cavity portion, and therefore, a monitoring condition becomes unstable. According to Patent Document 2, an observation region is limited to the inside of the esophageal region, and the existence of the bleeding inside the stomach cannot be monitored. According to Patent Document 3, there are problems that it is difficult to set a placement position of the medical capsule and if the medical capsule is to be fixed at a region where the inside of the stomach can easily be monitored, a scope for performing the clipping needs to be turned back for an operation, which is difficult. If the technology in Patent Document 2 is applied, the condition is the same as that in Patent Document 3.

The present invention is made in view of the above problems and an object of the present invention is to provide an in-vivo information acquiring apparatus, an in-vivo information acquiring system, and an in-vivo information acquiring method that enable to stably and properly monitor the inside of a body by using an easily operable placement technique.

Means for Solving Problem

An in-vivo information acquiring apparatus according to the present invention includes an in-vivo information acquiring apparatus main-body that is swallowed from an oral cavity of a subject to acquire in-vivo information of the subject and to wirelessly output the in-vivo information for a transmission to an outside of a body; a string member that is connected to the in-vivo information acquiring apparatus main-body to locate the swallowed in-vivo information acquiring apparatus main-body at a gastric cardia of the subject; and a fixing portion that is provided on a portion of the sting member to fix the string member to an esophageal region by an endoscopic fixture, the string member having located the in-vivo information acquiring apparatus main-body at the gastric cardia.

Further, an in-vivo information acquiring apparatus according to the present invention includes an in-vivo information acquiring apparatus main-body that acquires in-vivo information; and a string member extended from the in-vivo information acquiring apparatus main-body, wherein the string member includes an extracorporeal gripper that is provided to be located on an extracorporeal side from an oral cavity of a subject, in such an intragastric insertion state where the in-vivo information acquiring apparatus main-body is orally inserted into the subject and located inside a stomach, a marked portion that is located inside an esophageal region and indicates a fixing position of the sting member in the intragastric insertion state, a fixing portion that fixes the string member to an inner wall of the esophageal region, and a cutting portion that is provided at a position on the string member between the fixing portion or the marked portion and the extracorporeal gripper, and enables to cut the string member at the position.

Moreover, an in-vivo information acquiring apparatus according to the present invention includes an in-vivo information acquiring apparatus main-body that is swallowable by a subject; and a string member that includes a string member main-body extended from the in-vivo information acquiring apparatus main-body, an extracorporeal gripper that is provided on an extended end portion of the string member main-body, a fixing portion that is provided on a side of an extended rear anchor from the extracorporeal gripper on the string member main-body to enable to fix the string member main-body, a marked portion that enables to visually distinguish the fixing portion from the string member main-body, and a cutting portion that is provided at a position on the side of an extended end portion from the fixing portion on the string member main-body and enables to cut the string member main-body at the position.

In the in-vivo information acquiring apparatus according to the invention as set forth above, the fixing portion may be located at a position where a length from the connected in-vivo information acquiring main-body corresponds to a length from the gastric cardia to the inside of the esophageal region of the subject.

In the in-vivo information acquiring apparatus according to the present invention as set forth above, the in-vivo information acquiring apparatus main-body may detect at least an existence of a bleeding inside the stomach of the subject as in-vivo information to be acquired.

In the in-vivo information acquiring apparatus according to the present invention as set forth above, the in-vivo information acquiring apparatus main-body may be a capsule endoscope.

In the in-vivo information acquiring apparatus according to the present invention as set forth above, the in-vivo information acquiring apparatus main-body may be a hemoglobin sensor that detects the existence of the bleeding inside the stomach based on an adhesion of blood.

In the in-vivo information acquiring apparatus according to the present invention as set forth above, the in-vivo information acquiring apparatus main-body may be a red detection sensor.

In the in-vivo information acquiring apparatus according to the present invention as set forth above, the in-vivo information acquiring apparatus main-body may be configured to be thicker than a thickness of the string member.

In the in-vivo information acquiring apparatus according to the present invention as set forth above, the string member may be connected to an end portion of the in-vivo information acquiring apparatus main-body, and the in-vivo information acquiring apparatus main-body may have a reduced diameter shape with which a diameter of the in-vivo information acquiring apparatus main-body becomes smaller toward an end portion thereof to which the string member is connected.

The in-vivo information acquiring apparatus according to the present invention may further include a retaining member that engages and retains the in-vivo information acquiring apparatus main-body, wherein the string member may connected to the in-vivo information acquiring apparatus main-body via the retaining member.

In the in-vivo information acquiring apparatus according to the present invention as set forth above, the string member may be made of a material to be digested by gastric fluid.

In the in-vivo information acquiring apparatus according to the present invention as set forth above, the fixing portion may be located at a position to be fixed to the esophageal region at an upper portion from a lower esophageal sphincter.

In the in-vivo information acquiring apparatus according to the present invention as set forth above, the fixing portion may be located at a position to be fixed to the esophageal region between a lower esophageal sphincter and an upper esophageal sphincter.

In the in-vivo information acquiring apparatus according to the present invention as set forth above, the fixing portion may be in a latch shape for latching the endoscopic fixture.

In the in-vivo information acquiring apparatus according to the present invention as set forth above, the fixing portion may be provided at a plurality of portions of the string member.

In the in-vivo information acquiring apparatus according to the present invention as set forth above, the in-vivo information acquiring apparatus main-body may include a reel portion that reels out and reels off the string member.

An in-vivo information acquiring system according to the present invention includes an in-vivo information acquiring apparatus; a receiving device that receives in-vivo information wirelessly output and transmitted from an in-vivo information acquiring apparatus main-body; and a display device that displays the in-vivo information received by the receiving device.

An in-vivo information acquiring method according to the present invention includes swallowing an in-vivo information acquiring apparatus main-body to make a state where the in-vivo information acquiring apparatus main-body travels through an esophageal region and a gastric cardia and is hung down inside a stomach, the in-vivo information acquiring apparatus main-body being connected to a string member to acquire in-vivo information of a subject and to output the in-vivo information for a transmission to an outside; locating the in-vivo information acquiring apparatus main-body at the gastric cardia by pulling and loosening the string member to shift the in-vivo information acquiring apparatus main-body up and down, the in-vivo information acquiring apparatus main-body being hung down inside the stomach; fixing the string member to the esophageal region by an endoscopic fixture; transmitting in-vivo information acquired from the in-vivo information acquiring apparatus main-body to an outside of a body wirelessly; and cutting a lower stomach side of the string member fixed at the fixing.

The in-vivo information acquiring method according to the present invention may further include cutting an upper oral-cavity side of the string member fixed at the fixing to remove the cut upper oral-cavity side of the string member to an outside of a body.

The in-vivo information acquiring method according to the present invention may further include retrieving the in-vivo information acquiring apparatus main-body that is cut at the cutting and placed inside the stomach, to an outside of a body by a scooping.

The in-vivo information acquiring apparatus according to the present invention further includes the step of: retrieving the in-vivo information acquiring apparatus main-body that is cut at the cutting step and placed inside the stomach, to an outside of a body by a scooping.

Effect of the Invention

According to the in-vivo information acquiring apparatus, the in-vivo information acquiring system, and the in-vivo information acquiring method of the present invention, it becomes possible to stably and properly monitor the inside of a body by fixing a placement condition of an in-vivo information acquiring apparatus main-body that is to be inserted from an oral cavity for acquiring in-vivo information of a subject.

EXPLANATIONS OF LETTERS OR NUMERALS

100 Intragastric bleeding-existence detector
101 Capsule endoscope
102 End portion
103 String member
103a String-member main body
103b Extracorporeal gripper
103c Marked portion
103d Cutting portion
104 Fixing portion
111 Reel portion
200 Oral cavity
201 Subject
202 Gastric cardia
203 Esophageal region
204 Stomach
205 Lower esophageal sphincter
206 Upper esophageal sphincter
301 Receiving device
302 Display device
501 Retaining member
502 Capsule endoscope
601 Hemoglobin sensor
611 Red detection sensor

BEST MODE(S) FOR CARRYING OUT THE INVENTION

Exemplary embodiments of an in-vivo information acquiring apparatus, an in-vivo information acquiring system, and an in-vivo information acquiring method of the present invention will be described below with reference to the accompanying drawings. The present invention is not limited to the below embodiments. In a description of the drawings, same reference numerals are assigned to same components.

Figure 1:
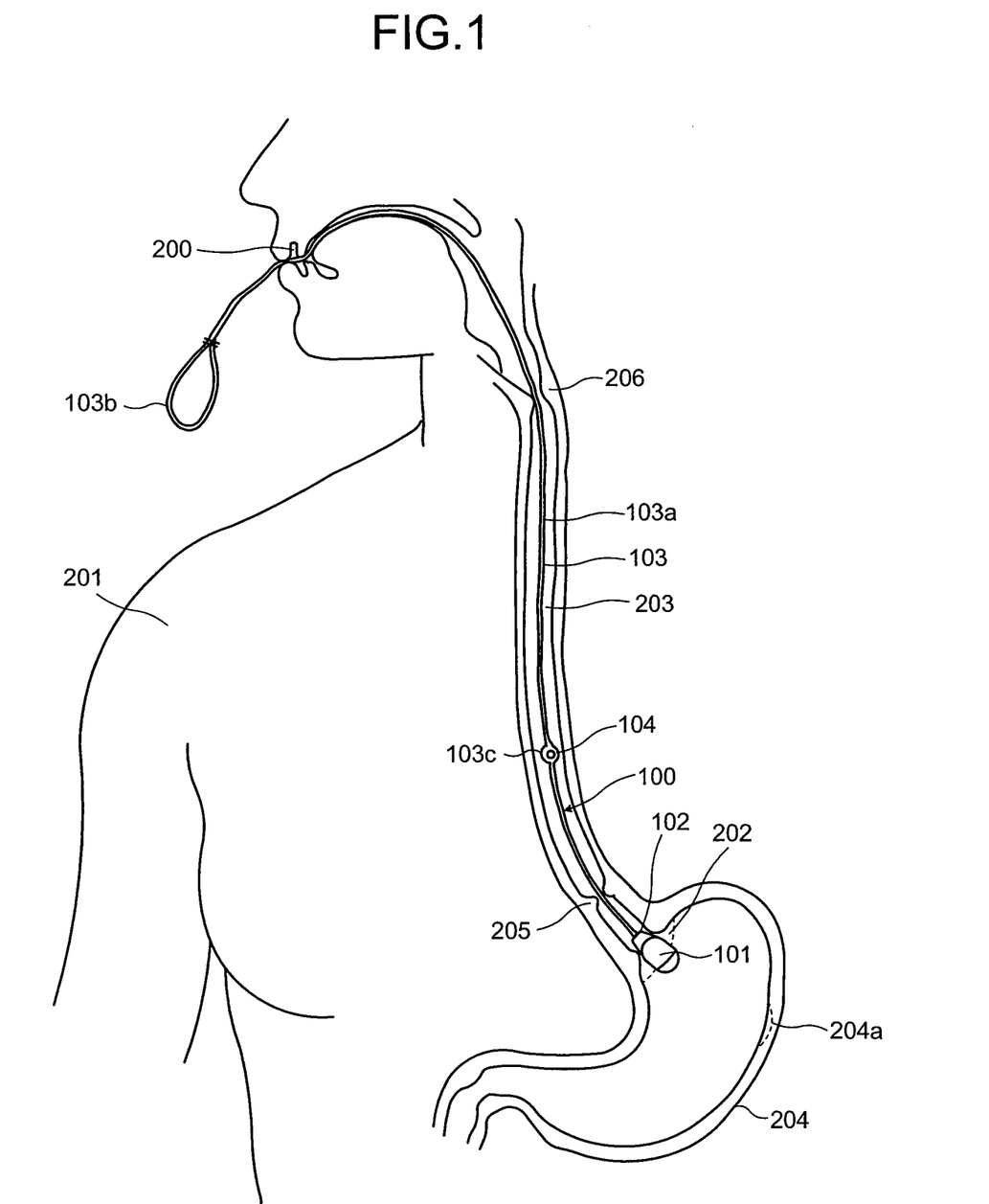
FIG. 1 is a schematic view for describing an example of applying an in-vivo information acquiring apparatus to an intragastric bleeding-existence detector and an initial state of an insertion thereof into a body cavity.

An embodiment of the present invention is described. FIG. 1 is a schematic view for describing an example of applying the in-vivo information acquiring apparatus to an intragastric bleeding-existence detector and an initial state of an insertion thereof into a body cavity. An intragastric bleeding-existence detector 100 includes a capsule endoscope 101, as an in-vivo information acquiring apparatus main-body, to be swallowed from an oral cavity 200 and inserted into a body cavity of a subject 201 to capture a body cavity image as body cavity information, and to wirelessly output data transmission of the captured body cavity image for a transmission, a string member 103 that is connected to an end portion 102 of the capsule endoscope 101 and locates the capsule endoscope 101 swallowed inside the body cavity at a gastric cardia 202 of the subject 201, and a fixing portion 104 that is provided on a portion of the string member 103 for fixing the string member 103 that has located the capsule endoscope 202 at the gastric cardiac 202 to body tissue (esophageal inner wall) inside an esophageal region 203 by an endoscopic fixture such as a clip described later.

The string member 103 connected to the end portion 102 of the capsule endoscope 101 includes a string-member main body 103a having an adequate length for extracting thereof from a stomach 204 to an outside via the oral cavity 200. In other words, the string member 103 includes an extracorporeal gripper 103b at an extended end portion of the string-member main body 103a on an extracorporeal side from the oral cavity 200, in such an intragastric insertion state that the capsule endoscope 101 is orally inserted by the subject 201 and located inside the stomach. It is preferable to make the string member 103 as thin as possible as long as it can easily be cut by a scissor forceps and the like described later and is strong.

The fixing portion 104 is formed in a pinhole shape as a simple latch shape to latch the clip described later in the middle of the string-member main body 103a, and also used as a marked portion 103c that is located inside the esophageal region 203 for enabling to visually distinguish the fixing portion 104 from the string-member main body 103a, in the intragastric insertion state in which the capsule endoscope 101 is located inside the stomach. The fixing portion 104 is provided on a position on which a length from the capsule endoscope 101 to which the string member 103 is connected corresponds to a length from the gastric cardiac 202 to the esophageal region 203 of the subject 201. More specifically, the fixing portion 104 is provided on the position to be fixed to the body tissue inside the esophageal region 203 by the clip, between a lower esophageal sphincter 205 and an upper esophageal sphincter 206.

The capsule endoscope 101 is configured to be thicker than the thickness of the string-member main body 103a and swallowable from the oral cavity 200, and is formed in a tapered reduced diameter shape with which a diameter becomes smaller toward the end portion 102 on the side of the end portion 102 to be connected to the string member 103. The reduced diameter shape is not limited to the tapered shape and a semispherical-dome shape similar to a front end portion can be acceptable.

Figure 7:
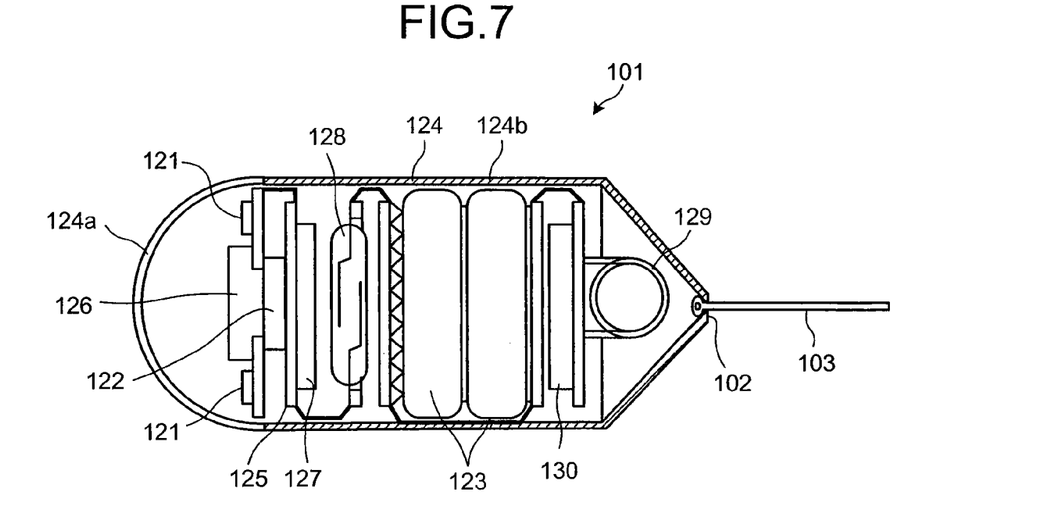
FIG. 7 is a sectional view for describing an internal configuration of the capsule endoscope.

The capsule endoscope 101 is described with reference to FIG. 7. FIG. 7 is a sectional view for describing an internal configuration of the capsule endoscope 101. The capsule endoscope 101 is configured to accommodate a capsule case 124, a plurality of illuminating units 121 such as a light emitting diode (LED) for illuminating a region inside the body cavity of the subject 201, an imaging element 122 such as a charge coupled device (CCD) or a complementary metal-oxide-semiconductor (CMOS) that captures the body cavity image, and a button type battery 123 that supplies electric power to the illuminating unit 121 and the imaging element 122. The battery 123 can be a silver oxide battery, a rechargeable battery, a generator battery and the like.

The capsule case 124 includes a transparent semispherical-dome shaped front-end cover case 124a that covers the illuminating unit 121 and a cylindrical-shaped body case 124b that is watertightly provided with the front-end cover case 124a and accommodates the battery 123, and is formed in a size swallowable from the oral cavity 200 of the subject 201. The body case 124b is made of a color material that is optically impermeable.

The imaging element 122 is implemented on an imaging board 125 and an optical system 126 such as an imaging lens is provided on a front surface of the imaging element 122. The imaging board 125 implements a controller 127 that processes or controls each of units, on a rear surface thereof.

The capsule endoscope 101 further accommodates a reed switch 128 that changes an ON/OFF state by an external magnetic filed, for controlling a drive of the capsule endoscope 101. The configuration is such that, the capsule endoscope 101 is installed in a package including a permanent magnet that supplies the external magnetic field in a storage condition, and the OFF sate is kept under a circumstance in which a magnetic field with a specific strength or above is provided, while it is to be the ON state when the strength of the external magnetic field decreases. Accordingly, when installed in the package, the capsule endoscope 101 is not to be activated.

The capsule endoscope 101 includes a transmitting device 130 with an antenna 129 attached on the rear side, which wirelessly outputs image information captured by the imaging element of the battery 123 to an outside. According to the present embodiment, an image inside the stomach 204 is optically captured as a color image by the imaging element 122 for serving to detect an existence of a bleeding site inside the stomach 204.

Figure 8:
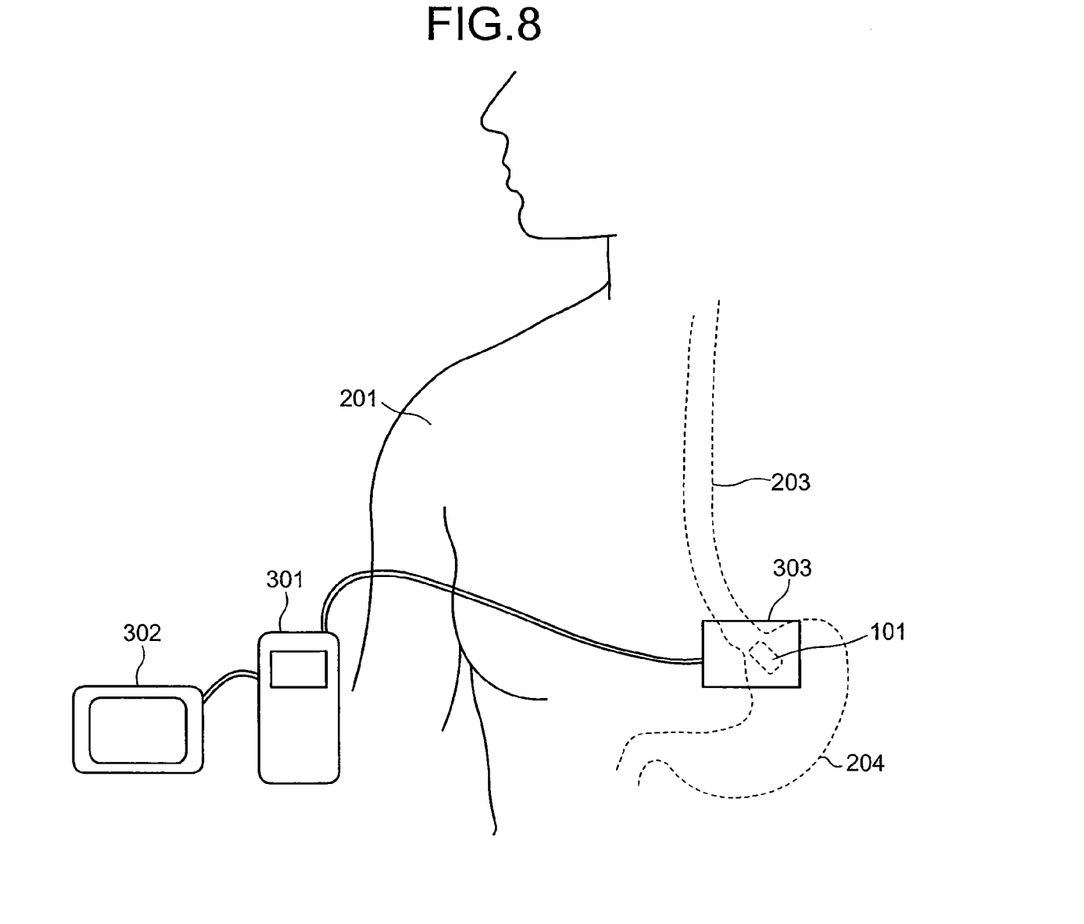
FIG. 8 is a schematic view for describing an example of a general configuration of a wireless intragastric bleeding-existence detecting system.

The intragastric bleeding-existence detector 100 including the above described capsule endoscope 101 structures an intragastric bleeding-existence detecting system as a medical system when combined with a receiving device and the like. FIG. 8 is a schematic view for describing an example of a general configuration of a wireless intragastric bleeding-existence detecting system. As shown in FIG. 8, the wireless intragastric bleeding-existence detecting system includes the capsule endoscope 101 that is to be inserted inside the subject 201 to capture the color image of the inside of the stomach 204 at a position of the gastric cardia 202 and to perform a data transmission of a picture signal by radio to a receiving device 301, the portable receiving device 301 that receives color image data wirelessly transmitted from the capsule endoscope 101, and a display device 302 such as a portable viewer that displays the color image based on the picture signal received by the receiving device 301. The receiving device 301 includes a receiving antenna 303 attached on the extracorporeal surface of the subject 201 around, for example, the gastric cardia 202.

A medical operation procedure including a placement of the capsule endoscope 101 inside the body cavity is sequentially described with reference to FIG. 1 to FIG. 6. The capsule endoscope 101 is swallowed and placed inside the body cavity for monitoring the existence of the bleeding site inside the stomach 204, after an endoscopic surgical procedure for the inside of the stomach 204 of the target subject 201 is finished. In FIG. 1 and other drawings, reference numeral 204a describes a surgical site of the endoscopic surgical procedure. The receiving antenna 303 is attached to the extracorporeal surface of the subject 201 at a proper timing before or after the capsule endoscope 101 is swallowed.

Firstly, as shown in FIG. 1, the capsule endoscope 101 to which the string member 103 is connected is swallowed from the oral cavity 200 and inserted until the capsule endoscope 101 is hung down inside the stomach 204 via the esophageal region 203 and the gastric cardia 202. At this state, the extracorporeal gripper 103b on the front end side of the string member 103 is positioned at the extracorporeal side from the oral cavity 200 for enabling a pulling/loosening operation outside the oral cavity 200.

Figure 2:
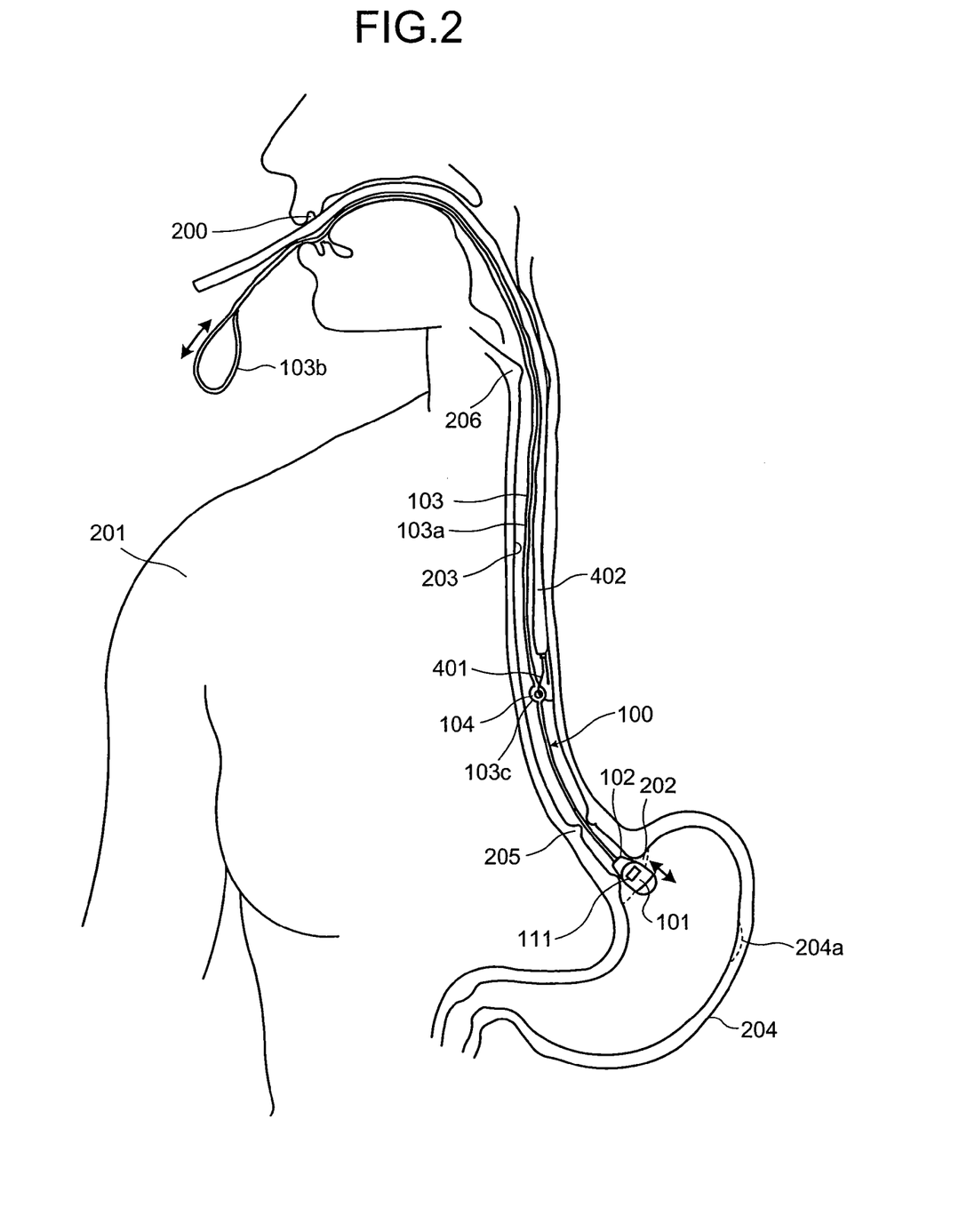
FIG. 2 is a schematic view for describing a condition of a pulling/loosening operation and a clip fixing of a string member.

Next, as shown in FIG. 2, by shifting the capsule endoscope 101 swallowed inside the stomach 204 up and down if necessary through the pulling/loosening operation of the extracorporeal gripper 103b of the string member 103 as an extraoral operation, the capsule endoscope 101 is located at the position of the gastric cardia 202. At this state, the end portion 102 on the side of the string member 103 of the capsule endoscope 101 is in tapered diameter-reduced portion and fits to a shape of a cardia that joins the stomach 204 and the esophageal region 203. Therefore, it is easy to position the capsule endoscope 101 to the gastric cardia 202 in such a state that the front-end cover case 124a becomes downward by pulling the string member 103, and the capsule endoscope 101 can easily be in a stable position. The gastric cardia 202 is a site from which the entire inside of the stomach 204 is easily inspected, and by locating the capsule endoscope 101 downwardly at the gastric cardia 202, it becomes possible to properly monitor the existence of the bleeding site inside the stomach 204 including the surgical site 204a. Further, because the capsule endoscope 101 is thicker than the string member 103, unless excessive pulling force is exerted, the capsule endoscope 101 is not extracted to the side of the esophageal region.

It is acceptable to perform an up/down movement of the capsule endoscope 101 not by the pulling/loosening operation of the extracorporeal gripper 103b but by using a reel portion 111 provided in the capsule endoscope 101. The reel portion 111 is for reeling out and reeling up the extracorporeal gripper 103b and enables to shift the capsule endoscope 101 up and down without shifting the string member 103. More specifically, the reel portion 111 includes a not shown rotary member that reels out and reels up the string member 103 and a not shown magnet that rotates the rotary member by an external rotary magnetic field generated outside the subject 201, and reels out and reels up the string member 103 in conjunction with the rotation of the magnet. Alternately, the reel portion 111 can be connected to the rotary member, include a not shown driving unit that rotates the rotary member, and perform a drive control of the driving unit by receiving an external control signal including the magnetic field. In both cases, because the capsule endoscope 101 by itself reels out and reels up the string member 103 and the string member 103 does not shift, it becomes possible to locate the capsule endoscope 101 at the gastric cardia 202 without injuring a pharyngeal portion.

Before or after performing an operation of locating the capsule endoscope 101 to the gastric cardia 202, an endoscope 402 that loads a clip 401 as the endoscopic fixture on a forceps channel is inserted inside the esophageal region 203 of the subject 201. Thereafter, with the capsule endoscope 101 located at the gastric cardia 202, the extraoral operation for the forceps channel of the endoscope 402 is performed for performing a clipping operation to find the pinhole shaped marked portion 103c and the fixing portion 104 for latching the clip 401 to fix the fixing portion 104 to the body tissue inside the esophageal region 203. Prior to the clipping, it is acceptable to check whether the capsule endoscope 101 is located at the gastric cardia 202 in a desired posture, by monitoring a captured image of the capsule endoscope 101 through the receiving device 301 and the display device 302.

With the capsule endoscope 101 located at the gastric cardia 202 through the extraoral operation, the string member 103 is in a strained state and the like, and by fixing the fixing portion 104 as a portion of the string member 103 to the inside of the esophageal region 203 by the clip 401, the capsule endoscope 101 is stably placed at the gastric cardia 202. In other words, when the capsule endoscope 101 is to be placed at the gastric cardia 202 from which the entire inside of the stomach 204 can be inspected, if it is directly fixed to the body tissue inside the stomach 104 by the endoscopic fixture, there is such a difficulty in an operation that the scope needs to be turned back. However, according to the present embodiment, although the capsule endoscope 101 itself is to be placed at the gastric cardia 202, the fixing is to be performed by using the fixing portion 104 of the string member 103 inside the esophageal region 203, which is easy. Further, since the fixing portion 104 is located to be fixed inside the esophageal region 203 other than such a movable site as the lower esophageal sphincter 205 and the upper esophageal sphincter 206, the posture of the capsule endoscope 101 after the fixing is less moved. Moreover, the endoscope 402 itself is basically required to be inserted into the esophageal region 203, inclusive of an operation described later, it is possible to reduce a burden of the subject 201 as much as possible.

Figure 3:
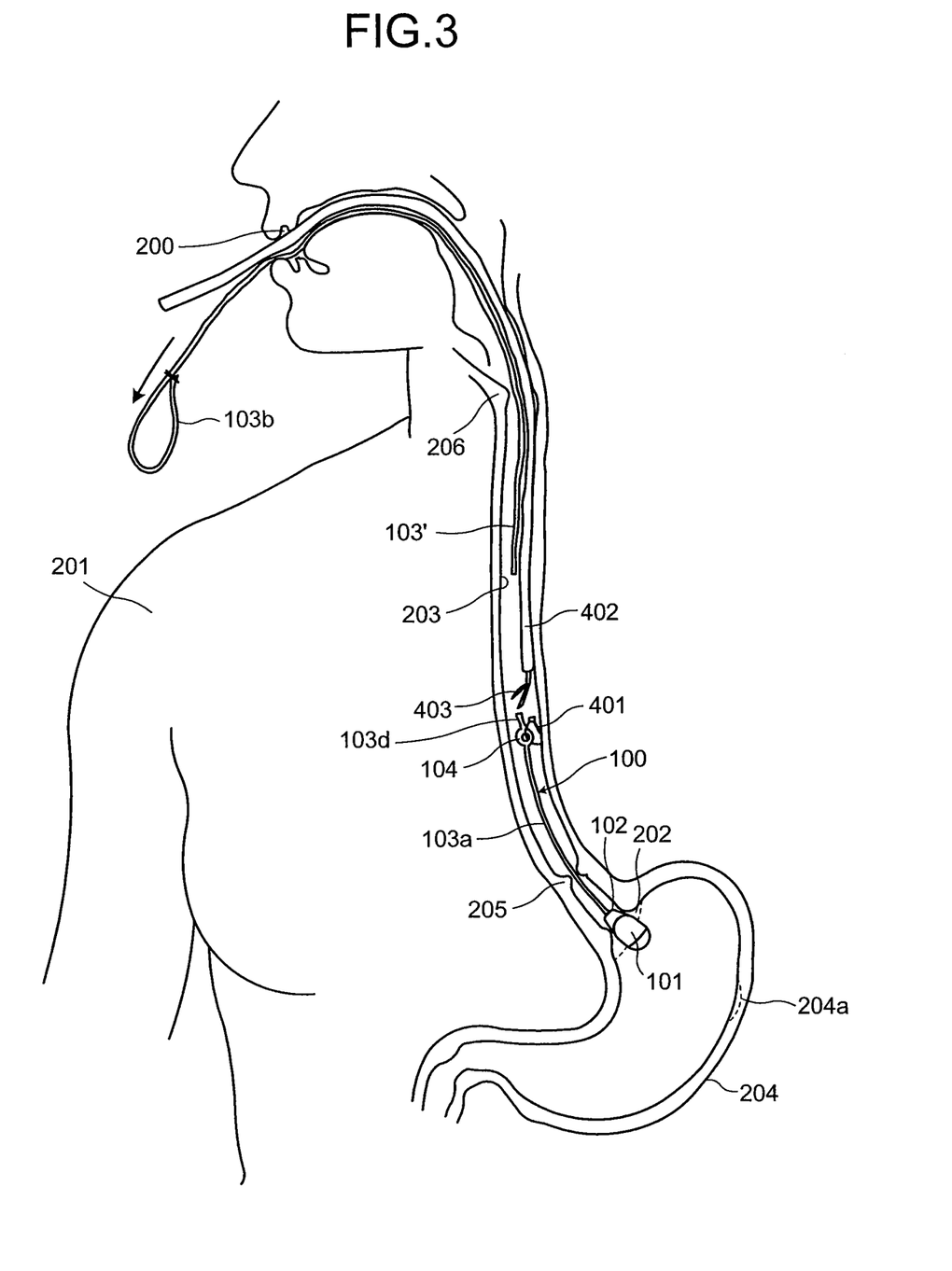
FIG. 3 is a schematic view for describing a condition of a cutting by a scissor forceps.
Figure 4:
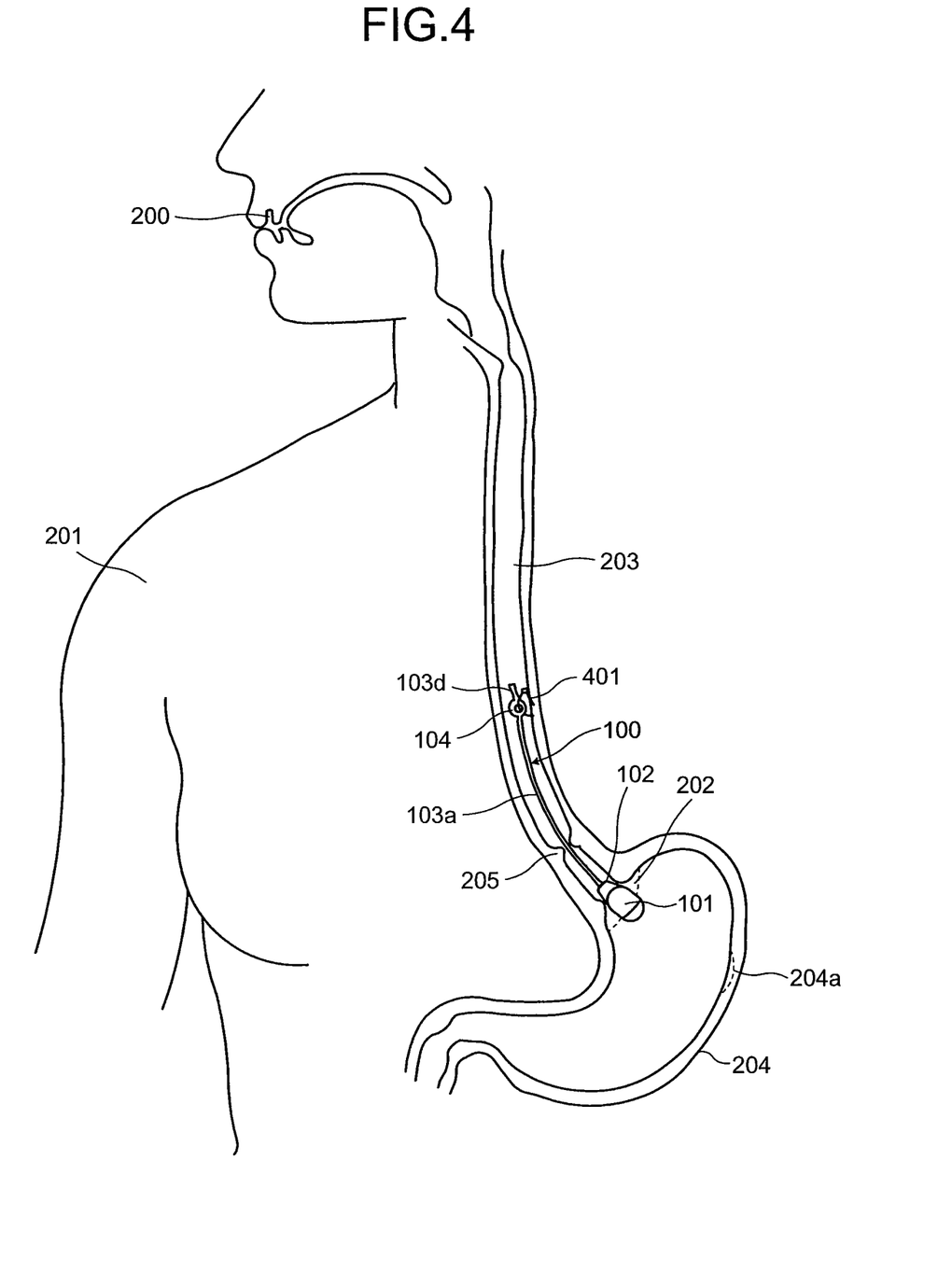
FIG. 4 is a schematic view for describing a final insertion condition of the string member and a capsule endoscope.

Next, as shown in FIG. 3, a scissor forceps 403 is inserted into the forceps channel of the endoscope 402 to cut the string member 103 at the upper portion of the fixing portion 104 fixed by the clip 401. In other words, the string member 103 according to the present embodiment includes a cutting portion 103d that is a portion on the side of the extracorporeal gripper 103b from the fixing portion 104 (the marked portion 103c) on the string-member main body 103a and that enables to cut the string-member main body 103a in the portion. The upper side of the string member 103 cut by the cutting portion 103d is removed to the outside of the body. Thereafter, as shown in FIG. 4, the endoscope 402 is also removed to the outside of the oral cavity. Accordingly, the intragastric bleeding-existence detector 100 becomes in a final condition with which the monitoring becomes enable by the capsule endoscope 101 placed at the gastric cardia 202 and the string member 103 fixed inside the esophageal region 203 by the fixing portion 104. Therefore, during a monitoring period after a surgery, the swallowable capsule endoscope 101 and the string member 103 are exclusively inserted in the body cavity of the subject 201, and there is less pain for the subject 201. If there is no harm in leaving the string member 103 inside the esophageal region 203 and the oral cavity 200, the operation of cutting the string member 103 can be omitted.

At this state, by enabling the intragastric bleeding-existence detecting system shown in FIG. 8, the existence of the bleeding site inside the stomach 204 after the surgery can be properly monitored. In other words, by capturing an image of the inside of the stomach 204 from the position of the gastric cardia 202 by the imaging element 122 at a proper cycle, by wirelessly outputting the captured color image for a transmission to the receiving antenna 303 via the controller 127, the transmitting device 130, and the transmitting antenna 129, and by outputting the color image received by the receiving antenna 303 for a display on the display device 302 by the receiving device 301, the existence of the bleeding site inside the stomach 204 after the surgery can be properly monitored.

Figure 5:
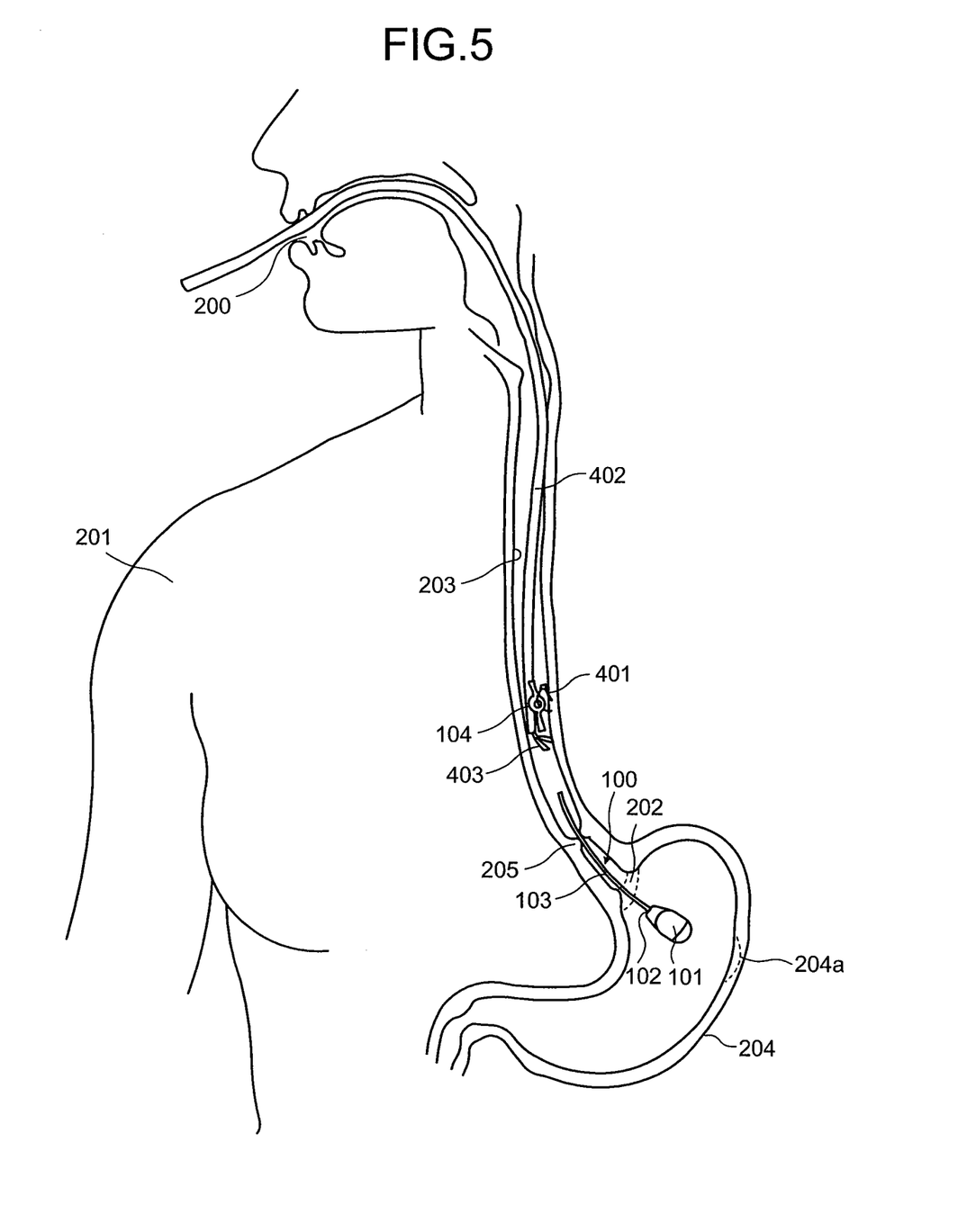
FIG. 5 is a schematic view for describing a condition of the cutting by the scissor forceps after a monitoring is finished.

If the monitoring of the existence of the bleeding site inside the stomach 204 after the surgery is finished, as shown in FIG. 5, the endoscope 402 is again inserted into the esophageal region 203 of the subject 201 to cut the string member 103 at a position below the fixing portion 104 by operating the scissor forceps 403 of the forceps channel, and the cut string member 103 is poured into the stomach 204 together with the capsule endoscope 101.

Figure 6:
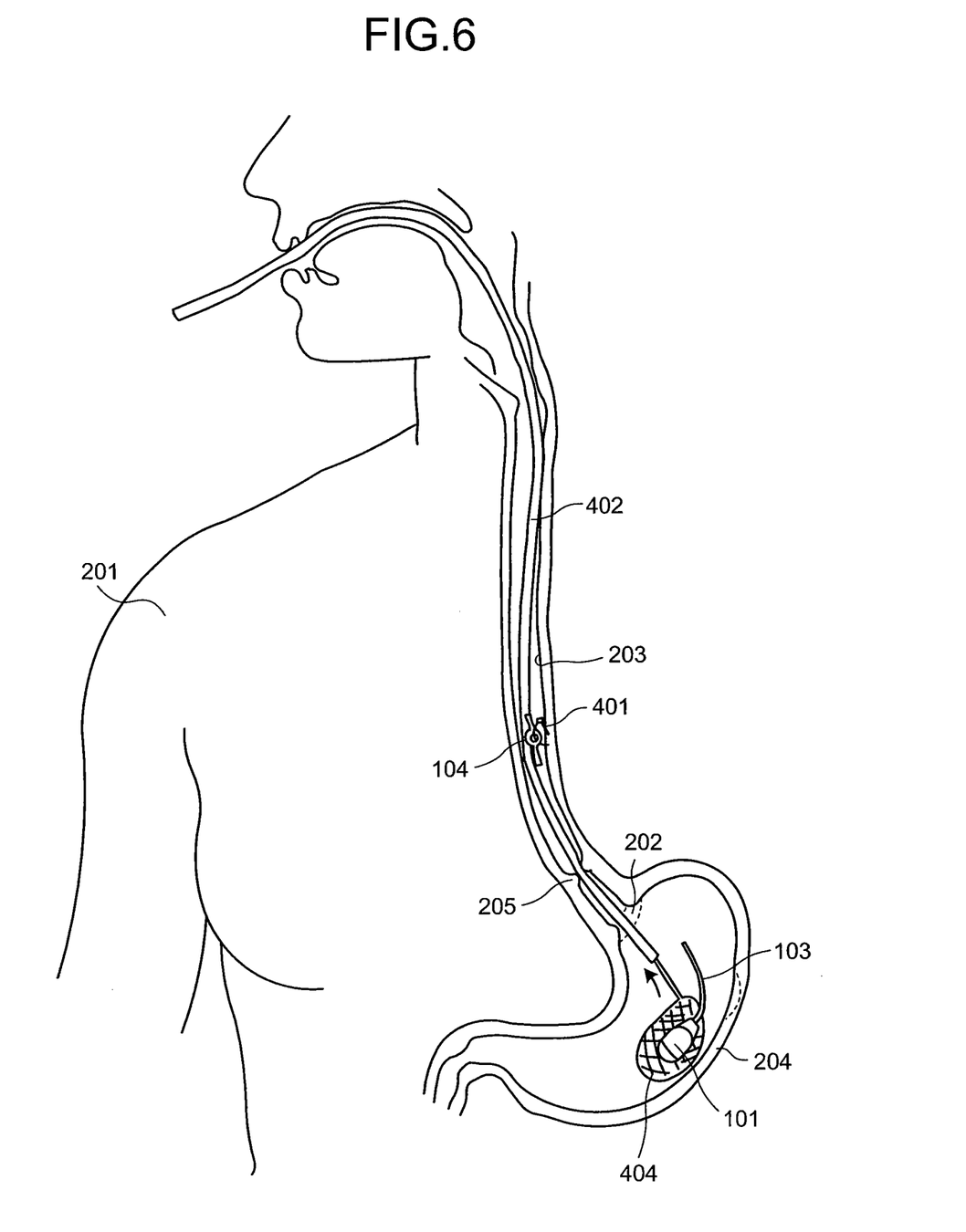
FIG. 6 is a schematic view for describing a condition of a retrieving by a retrieving net.

Further, the forceps channel of the endoscope 402 is replaced with a retrieving net 404 and, as shown in FIG. 6, the retrieving net 404 is inserted into the stomach 204 to scoop the capsule endoscope 101 and the string member 103 inside the stomach 204 and removed together with the endoscope 402 to the outside of the body, which ends a series of the operations. The fixing portion 104 fixed by the clip 401 is put into the stomach 204 by being dropped down along with a necrosis of the body tissue of the portion of the clip 401, and excreted to the outside of the body. If the string member 103 is made of a material to be digested by strongly acidic gastric fluid, the cut string member 103 is digested inside the stomach 204, and the remained capsule endoscope 101 is to be excreted to the outside of the body through a small intestine and a large intestine, the retrieving operation by the retrieving net 404 can be omitted.

Figure 9:
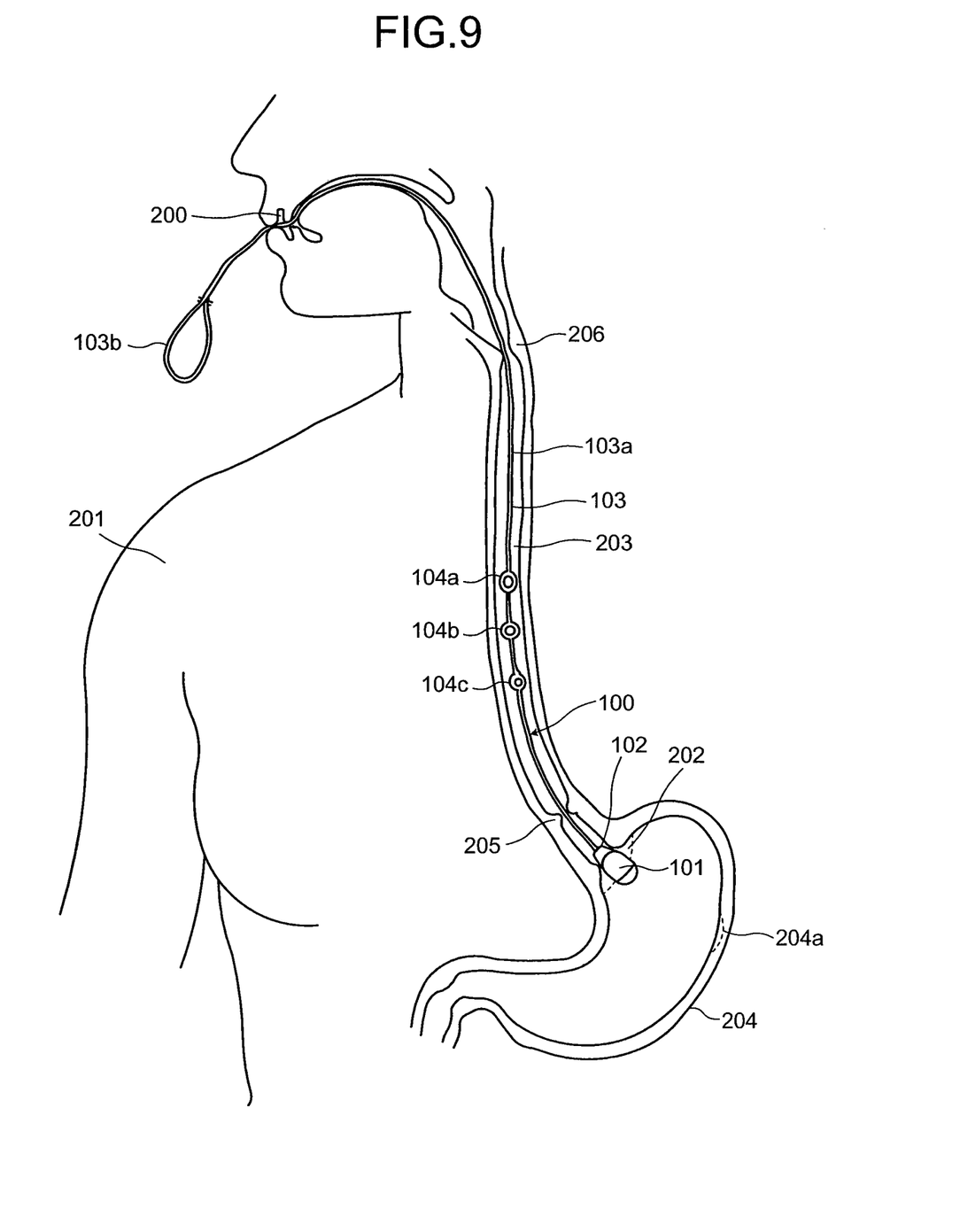
FIG. 9 is a schematic view for describing a condition of providing a plurality of fixing portions.

As shown in FIG. 9, it is acceptable to provide fixing portions 104a, 104b, 104c, . . . at a plurality of portions of the string member 103. Accordingly, when the fixing portion is fixed inside the esophageal region 203 by the clip 401, a portion at which the clipping is easily performed can be selected from among a plurality of the fixing portions 104a, 104b, 104c, . . . , which makes an operation effective.

Figure 10:
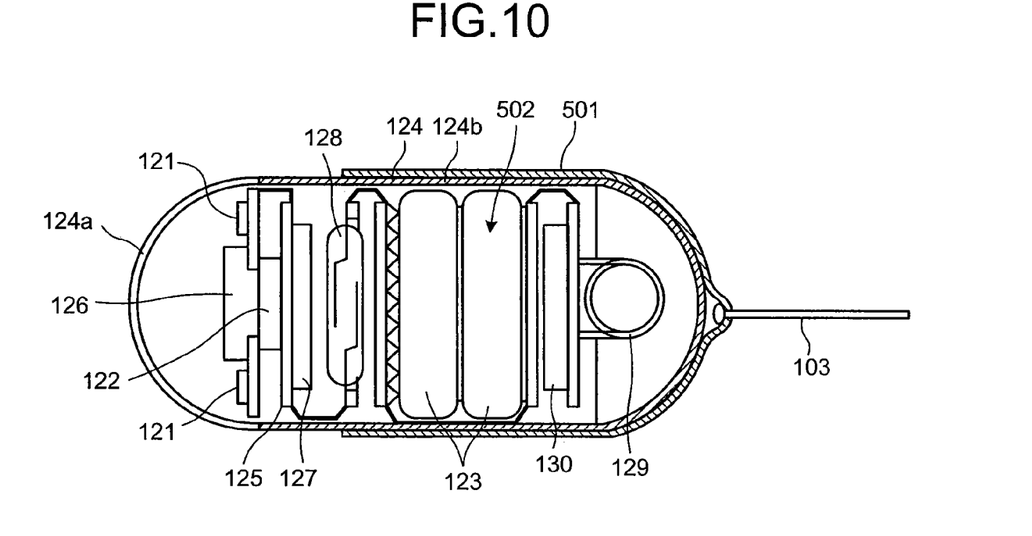
FIG. 10 is a sectional view for describing an internal configuration of a capsule endoscope in a type with a retaining member.

According to the present embodiment, the capsule endoscope 101 to which the string member 103 is directly connected is used. However, as shown in FIG. 10, such a capsule endoscope 502 can be used that is engaged and retained through a press fitting by a retaining member 501 to which the string member 103 is connected. In this case, the all-purpose capsule endoscope 502 that is mass produced as a capsule endoscope for a purpose of observing the small intestine and the like can be used and general versatility can be improved.

Figure 11:
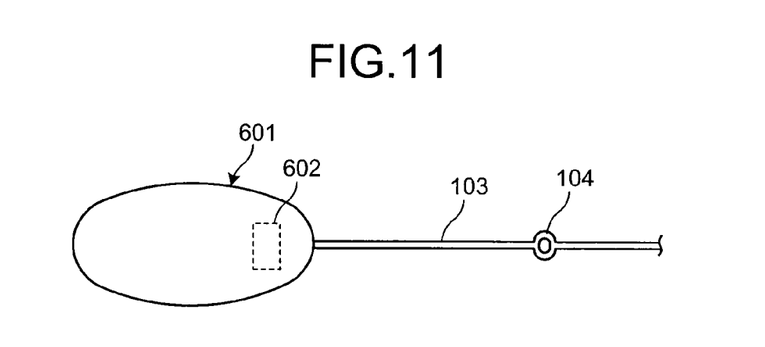
FIG. 11 is a schematic sectional view for describing an example of using a hemoglobin sensor as a sensor.
Figure 12:
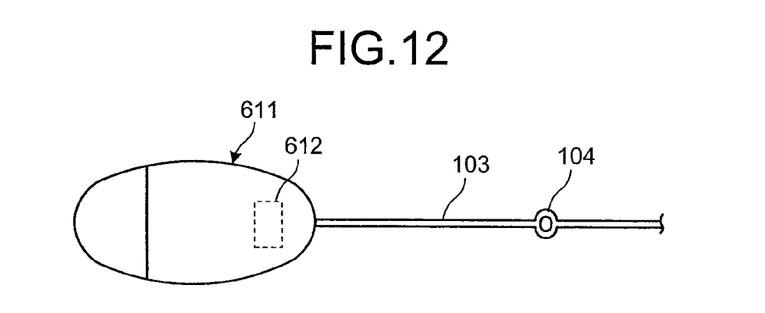
FIG. 12 is a schematic sectional view for describing an example of using a red detection sensor as the sensor.

Further, according to the present embodiment, the example in which the capsule endoscope 101 is used as the in-vivo information acquiring apparatus that monitors the inside of the stomach is described. However, a hemoglobin sensor 601 as shown in FIG. 11 or a red detection sensor 611 as shown in FIG. 12 can be used instead of the capsule endoscope 101. The hemoglobin sensor 601 detects the existence of the bleeding site by wirelessly performing a transmission output to the outside of a body through a wireless device 602, when blood in a specific amount or above is adhered to an outer surface. The red detection sensor 611 detects the existence of the bleeding site by wirelessly performing the transmission output to the outside of the body through a wireless device 612, when responding to red such as blood.

Figure 13:
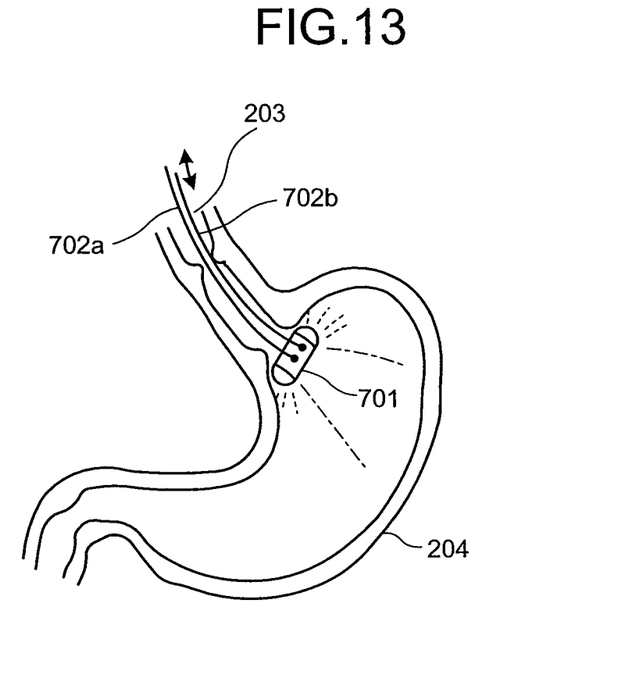
FIG. 13 is a schematic view for describing a condition of an adjustment when a plurality of the string members is used.

Moreover, according to the present embodiment, the one string member 103 is provided for the capsule endoscope as a configuration example. However, it is acceptable to connect a plurality of the string members at different connection points to make an angle adjustable. FIG. 13 describes an example in which such a binocular type capsule endoscope 701 is used that includes two imaging elements that can observe both a front direction and a rear direction, and two string members 702a and 702b, for example, are connected at the different connection points for the capsule endoscope 701. Accordingly, it is acceptable to make such a condition that the surgical site can be clearly viewed by determining a placement position of the capsule endoscope 701 by, for example, the one string member 702a, and thereafter, adjusting the angle of the capsule endoscope 701 by pulling or loosening the other string member 702b. The above can also be applicable to a monocular type shown in FIG. 7 and FIG. 10.

The present invention is not limited to the above described embodiments, and various modifications can be acceptable without departing a scope and a spirit of the present invention.

INDUSTRIAL APPLICABILITY

As described above, the in-vivo information acquiring apparatus, the in-vivo information acquiring system, and the in-vivo information acquiring method according to the present invention are suitable for properly performing a monitoring of the inside of a body by using an easily operable placement technique, and more specifically suitable for a type using a capsule endoscope.

The invention claimed is:

1. An in-vivo information acquiring apparatus comprising:
an in-vivo information acquiring apparatus main-body configured to be swallowed from an oral cavity of a subject and inserted into a body cavity of the subject to acquire in-vivo information of the subject and to wirelessly output the in-vivo information for a transmission to an outside of the body cavity, the in-vivo information acquiring apparatus main-body including an end portion having a tapered diameter-reduced portion configured to fit to a shape of a cardia joining a stomach and an esophageal region so as to monitor an existence of a bleeding inside the stomach of the subject based on the acquired in-vivo information;
a string member connected to the end portion of the in-vivo information acquiring apparatus main-body to locate the swallowed in-vivo information acquiring apparatus main-body inside the body cavity at a gastric cardia of the subject, the string member including a string member main body having an adequate length for extracting thereof from the stomach of the subject to an outside via the oral cavity, and an extracorporeal gripper at an extended end portion of the string member main body on an extracorporeal side from the oral cavity; and
a fixing portion provided on a portion of the string member main body and configured to be fixed to an inside of the esophageal region other than at a lower esophageal sphincter and an upper esophageal sphincter by an endoscopic fixture when the string member main body is cut at a position on the string member between the fixing portion and the extracorporeal gripper, the string member having located the in-vivo information acquiring apparatus main-body at the gastric cardia, and the fixing portion being formed in a pinhole shape for latching the endoscopic fixture and having a marked portion located inside the esophageal region for enabling visual distinguishing of the fixing portion from the string member main body,
wherein the fixing portion is located at a position where a length from the connected in-vivo information acquiring apparatus main-body corresponds to a length from the gastric cardia to the inside of the esophageal region of the subject.

2. The in-vivo information acquiring apparatus according to claim 1, wherein the in-vivo information acquiring apparatus main-body includes a capsule endoscope.

3. The in-vivo information acquiring apparatus according to claim 1, wherein the in-vivo information acquiring apparatus main-body includes a hemoglobin sensor configured to detect the existence of the bleeding inside the stomach based on an adhesion of blood.

4. The in-vivo information acquiring apparatus according to claim 1, wherein the in-vivo information acquiring apparatus main-body is a red detection sensor.

5. The in-vivo information acquiring apparatus according to claim 1, wherein the in-vivo information acquiring apparatus main-body is configured to be thicker than a thickness of the string member.

6. The in-vivo information acquiring apparatus according to claim 1, further comprising:
a retaining member that engages and retains the in-vivo information acquiring apparatus main-body, wherein the string member is connected to the in-vivo information acquiring apparatus main-body via the retaining member.

7. The in-vivo information acquiring apparatus according to claim 1, wherein the string member is made of a material to be digested by gastric fluid.

8. The in-vivo information acquiring apparatus according to claim 1, wherein the fixing portion is located at a position to be fixed to the esophageal region between a lower esophageal sphincter and an upper esophageal sphincter.

9. The in-vivo information acquiring apparatus according to claim 1, wherein the fixing portion is provided at a plurality of portions of the string member.

10. The in-vivo information acquiring apparatus according to claim 1, wherein the in-vivo information acquiring apparatus main-body includes a reel portion that reels out and reels off the string member.

11. An in-vivo information acquiring system comprising:
an in-vivo information acquiring apparatus that includes an in-vivo information acquiring apparatus main-body configured to be swallowed from an oral cavity of a subject and inserted into a body cavity of the subject to acquire in-vivo information of the subject and to wirelessly output the in-vivo information for transmission to an outside of the body cavity, the in-vivo information acquiring apparatus main-body including an end portion having a tapered diameter-reduced portion configured to fit to a shape of a cardia joining a stomach and an esophageal region so as to monitor an existence of a bleeding inside the stomach of the subject based on the acquired in-vivo information, a string member connected to the end portion of the in-vivo information acquiring apparatus main-body to locate the swallowed in-vivo information acquiring apparatus main-body inside the body cavity at a gastric cardia of the subject, the string member including a string member main body having an adequate length for extracting thereof from the stomach of the subject to an outside via the oral cavity and an extracorporeal gripper at an extended end portion of the string member main body on an extracorporeal side from the oral cavity, and a fixing portion provided on a portion of the string member main body and configured to be fixed to an inside of the esophageal region other than at a lower esophageal sphincter and an upper esophageal sphincter by an endoscopic fixture when the string member main body is cut at a position on the string member between the fixing portion and the extracorporeal gripper, the string member having located the in-vivo information acquiring apparatus main-body at the gastric cardia, and the fixing portion being formed in a pinhole shape for latching the endoscopic fixture and having a marked portion located inside the esophageal region for enabling visual distinguishing of the fixing portion from the string member main body, wherein the fixing portion is located at a position where a length from the connected in-vivo information acquiring apparatus main-body corresponds to a length from the gastric cardia to the inside of the esophageal region of the subject;

a receiving device configured to receive the in-vivo information wirelessly output and transmitted from the in-vivo information acquiring apparatus main-body; and a display device configured to display the in-vivo information received by the receiving device.

12. The in-vivo information acquiring system according to claim 11, further comprising:

a retaining member that engages and retains the in-vivo information acquiring apparatus main-body, wherein the string member is connected to the in-vivo information acquiring apparatus main-body via the retaining member.

13. The in-vivo information acquiring system according to claim 11, wherein the fixing portion is provided at a plurality of portions of the string member.

14. The in-vivo information acquiring system according to claim 11, wherein the in-vivo information acquiring apparatus main-body includes a reel portion that reels out and reels off the string member.

* * * * *

UNITED STATES PATENT AND TRADEMARK OFFICE
CERTIFICATE OF CORRECTION

PATENT NO. : 8,491,464 B2  Page 1 of 1
APPLICATION NO. : 11/571510
DATED : July 23, 2013
INVENTOR(S) : Yokoi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1420 days.

Signed and Sealed this
Eighth Day of September, 2015

Michelle K. Lee
*Director of the United States Patent and Trademark Office*